United States Patent
Seifert

(10) Patent No.: US 11,950,908 B2
(45) Date of Patent: Apr. 9, 2024

(54) INTRA-MOLD STERILIZATION OF PLASTIC-EMBEDDED NEEDLE

(71) Applicant: FACET TECHNOLOGIES, LLC, Atlanta, GA (US)

(72) Inventor: Kevin J. Seifert, Concord, MA (US)

(73) Assignee: Facet Technologies, LLC, Atlanta, GA (US)

( * ) Notice: Subject to any disclaimer, the term of this patent is extended or adjusted under 35 U.S.C. 154(b) by 530 days.

(21) Appl. No.: 17/000,462

(22) Filed: Aug. 24, 2020

(65) Prior Publication Data

US 2020/0383619 A1 Dec. 10, 2020

Related U.S. Application Data

(62) Division of application No. 14/299,857, filed on Jun. 9, 2014, now Pat. No. 10,779,758.

(60) Provisional application No. 61/833,088, filed on Jun. 10, 2013.

(51) Int. Cl.
| | |
|---|---|
| B29C 45/14 | (2006.01) |
| A61B 5/15 | (2006.01) |
| A61B 5/151 | (2006.01) |
| B29L 31/00 | (2006.01) |

(52) U.S. Cl.
CPC ........ *A61B 5/151* (2013.01); *A61B 5/150022* (2013.01); *A61B 5/150274* (2013.01); *A61B 5/150282* (2013.01); *A61B 5/15032* (2013.01); *A61B 5/150412* (2013.01); *A61B 5/150503* (2013.01); *A61B 5/150541* (2013.01); *B29C 45/14598* (2013.01); *B29C 45/14778* (2013.01); *B29L 2031/753* (2013.01); *B29L 2031/7544* (2013.01)

(58) Field of Classification Search
CPC .................... B29C 45/14819; B29L 2031/753
See application file for complete search history.

(56) References Cited

U.S. PATENT DOCUMENTS

| | | |
|---|---|---|
| 2,836,942 A | 6/1958 | Miskel |
| 3,358,689 A | 12/1967 | Higgins |
| 4,128,613 A | 12/1978 | Allen |
| 4,812,116 A | 3/1989 | Abrams |
| 5,456,875 A | 10/1995 | Lambert |
| 5,527,334 A | 6/1996 | Kanner et al. |
| 6,102,927 A | 8/2000 | Wright |

(Continued)

FOREIGN PATENT DOCUMENTS

EP 0776633 A1 6/1997

OTHER PUBLICATIONS

Capitol Vial Molding Process; Lumur International, Inc .; 2004; 5 pgs.

(Continued)

*Primary Examiner* — Kevin Joyner
(74) *Attorney, Agent, or Firm* — Perilla Knox & Hildebrandt, LLP

(57) ABSTRACT

Methods for intra-mold sterilization of a plastic-embedded metal component of a product, such as a medical lancet having a metal needle embedded within a plastic lancet body. For example, a lancet needle is retained within a mold, plastic is injected to encapsulate the needle, and a specified minimum temperature is maintained for a specified minimum cycle time. In example forms, the specified minimum mold temperature is at least about 370 degrees Fahrenheit and the specified minimum cycle time is at least about 10 seconds.

9 Claims, 3 Drawing Sheets

(56) References Cited

U.S. PATENT DOCUMENTS 8,052,926 B2 11/2011 Joseph et al.
2007/0162064 A1 7/2007 Starnes

OTHER PUBLICATIONS

Molin, Goran; "Inactivation of Bacillus Spores in Dry Systems at Low and High Temperatures"; The Swedish Meat Research Cetre; Journal of General Microbiology (1977), vol. 101, pp. 227-231; Great Britain.
International Search Report & Written Opinion for PCT/US2014/041561; dated Sep. 15, 2014; 11 pgs.

INTRA-MOLD STERILIZATION OF PLASTIC-EMBEDDED NEEDLE

CROSS-REFERENCE TO RELATED APPLICATIONS

This application is a divisional of U.S. Non-Provisional Patent Application Ser. No. 14/299,857 filed Jun. 9, 2014, which claims the benefit of U.S. Provisional Patent Application Ser. No. 61/833,088 filed Jun. 10, 2013, the entireties of which are hereby incorporated herein by reference for all purposes.

TECHNICAL FIELD

The present invention relates generally to the field of manufacturing medical devices and components, and more particularly to methods for sterilizing a plastic-embedded needle or other object during the manufacturing thereof.

BACKGROUND

Medical devices and components used for transcutaneous applications are typically sterilized prior to use. In most cases, the sterilization of medical devices and components occurs in a post-manufacturing process after the manufacturing and assembly thereof. For example, many medical devices are sterilized by autoclaving. Some items, however, are not well suited to the heat required for autoclaving.

For example, medical lancets utilized for penetrating the skin of a human or animal subject to obtain a sample of blood typically include a metal needle embedded in a plastic lancet body. The sharp tip of the lancet is embedded in a protective plastic endcap that is molded together with the lancet body, typically as a unitary body having a thin frangible section to facilitate separation and removal of the endcap. The heat of autoclaving necessary to sterilize the metal needle would likely damage the plastic lancet body. As such, a standard practice in the industry is to sterilize lancets by delivery of gamma radiation through the lancets after manufacture. This method of sterilization typically requires considerable additional time and capital, leading to increased costs.

Many lancets are high-volume commodity products, where cost is a critical consideration. In order to minimize manufacturing costs, manufacturers traditionally have sought to shorten the in-mold cycle times of molding and de-molding lancets, since shorter cycle times typically allow higher production rates and thereby lower per-unit costs.

It is to the provision of improved manufacturing and sterilization methods that the present invention is primarily directed.

SUMMARY

In example embodiments, the present invention provides improved methods of manufacturing and sterilizing medical devices comprising plastic embedded metal components such as lancets. The method comprises an intra-mold sterilization process, wherein a metal component such as a lancet needle is disposed within a mold cavity, a plastic body is formed to encapsulate the metal component by injection molding, and maintaining the formed product in the mold at at least a specified mold temperature for at least a specified cycle time, effective to sterilize the metal component.

In another aspect, the invention relates to a method for simultaneously manufacturing and sterilizing a product. The method includes providing a tool; providing a portion of a medical device component within the tool; injecting a plastic within the tool to encapsulate the medical device component, the plastic being at a tool temperature; and maintaining the plastic at a specified minimum tool temperature for a specified minimum cycle time, effective to sterilize the metal component.

In still another aspect, the invention relates to a method for manufacturing a sterile lancet. The method includes providing a mold, the mold having a cavity; retaining a lancet needle within the cavity; injecting plastic within the cavity to encapsulate the needle therein, the plastic having a mold temperature; and maintaining the plastic at the mold temperature for a cycle time, effective to sterilize the metal component.

In another aspect, the invention relates to a sterile product manufactured according to any of the methods described herein, for example a sterile lancet so manufactured.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Generally described, the present invention relates to methods for sterilizing a plastic-embedded needle or other metal component of a plastic-embedded product. In example forms, the plastic-embedded needle is in the form of a lancet comprising a generally elongate needle entirely encapsulated within a plastic body wherein a sharp tip portion of the needle is embedded in a removable plastic cap. The lancet is preferably manufactured by utilizing a mold or tool wherein plastic can be injected within a cavity defined therein to form the lancet. The needle is placed within the cavity of the mold and the plastic injected therein entirely encapsulates the needle. The plastic being injected therein is preferably delivered at or heated to a specified temperature and maintains that specified temperature for a specified amount of time. Thus, by maintaining the plastic at a specified temperature for a specified amount of time within the cavity of the mold, the needle that is encapsulated within the plastic body is sterilized, which eliminates the need for post-manufacturing sterilization.

Figure 1:
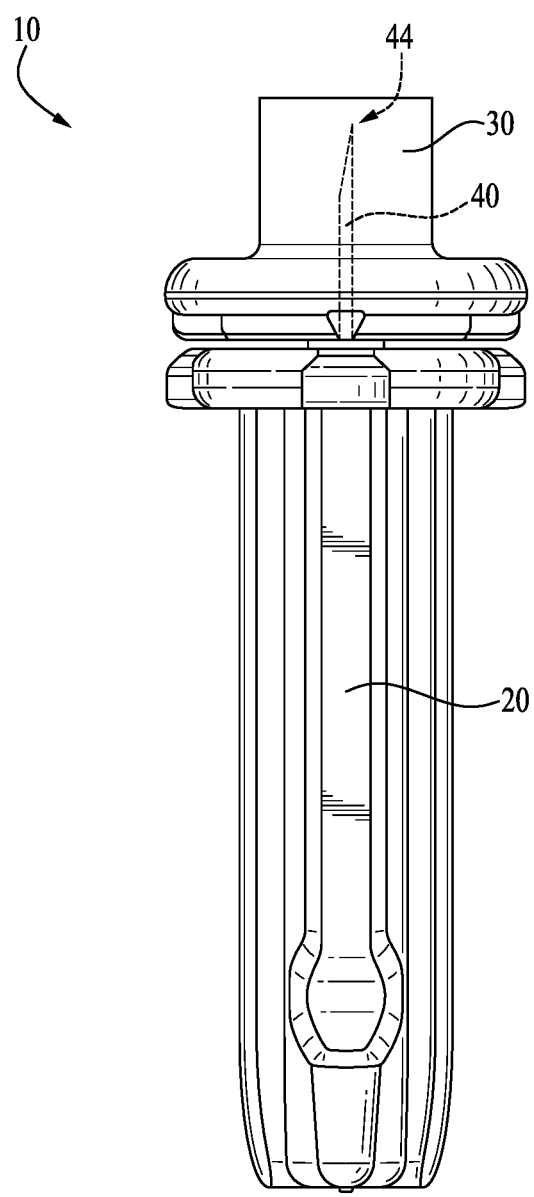
FIG. 1 is a side view of a lancet formed according to an example embodiment of the present invention.

With reference now to the drawing figures, wherein like reference numbers represent corresponding parts throughout the several views, FIG. 1 shows a plastic-embedded needle or lancet 10 comprising a sterile needle 40, according to an example form of the present invention. The lancet 10 includes a generally elongate body comprising a body portion 20, a removable cap 30, and the needle 40 having a sharp tip portion 44. The body portion 20 and the removable cap 30 entirely or substantially entirely encapsulate the needle or lancing needle 40 embedded therein (i.e., no portion of the needle that contacts the lancing site when the lancet is used is exposed externally of the plastic overmolding after manufacture, prior to removal of the endcap for use of the lancet). Preferably, the body portion 20 and the removable cap 30 are integrally formed as a single continuous molding, such that the needle 40 is entirely encapsulated therein. The needle can be a pointed tip type or a blade tip type needle.

Figure 2:
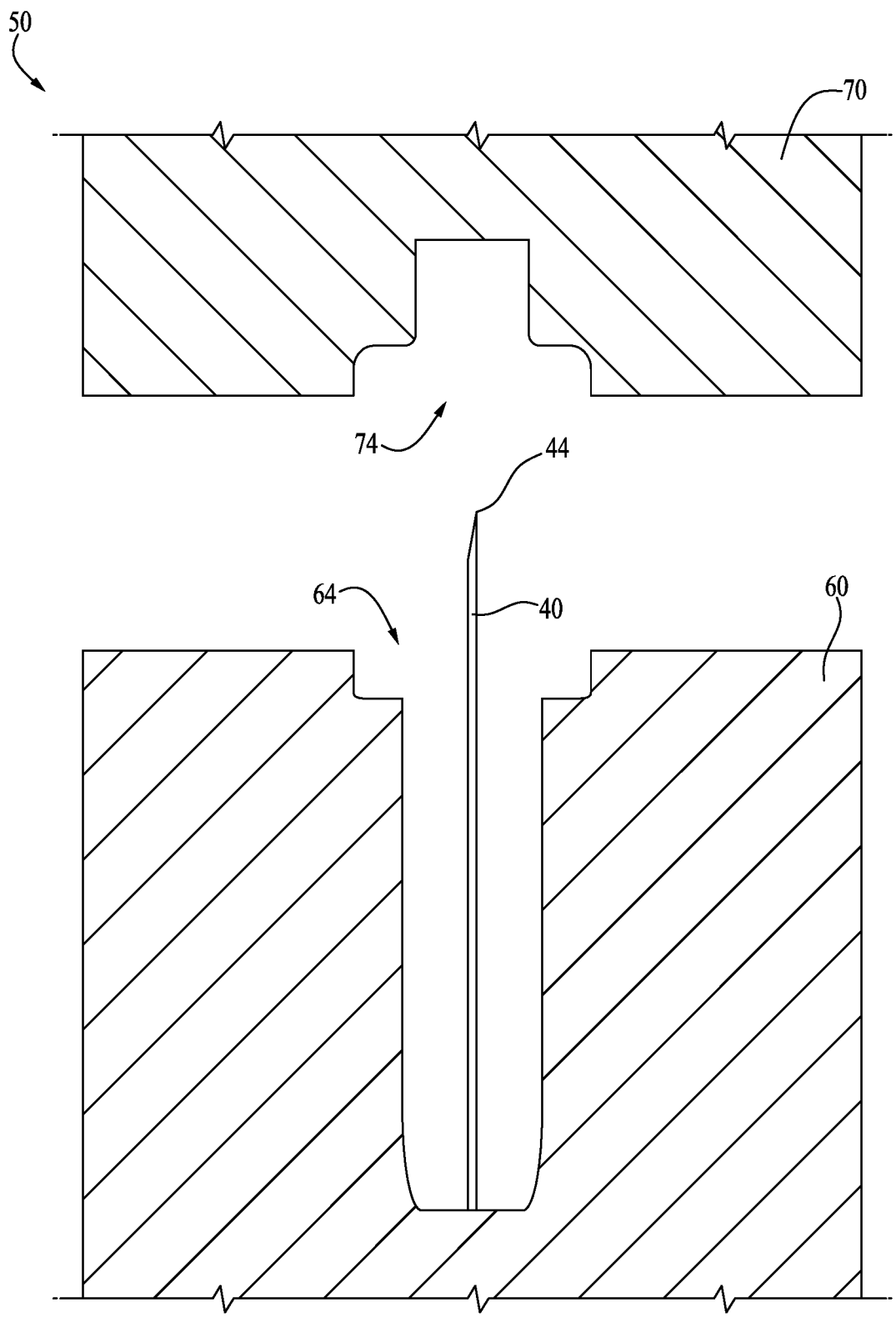
FIG. 2 shows a cross sectional view of a mold in the open position according to an example embodiment of the present invention, and showing a needle placed within a portion of a cavity thereof.

FIG. 2 shows a mold or tool 50 in an open position according to an example embodiment of the present invention. Preferably, the mold 50 is utilized to manufacture the lancet 10. In example forms, the mold 10 comprises a first mold part 60 and a second mold part 70. The first mold part 60 comprises a first cavity 64 and the second mold part 70 comprises a second cavity 74. Generally, the first and second cavities 64, 74 are sized, shaped and formed accordingly to form the body portion 20 and removable cap 30, respectively to be produced. Preferably, the needle 40 is placed substantially within the first cavity 64 of the first mold part 60 to be encapsulated by the body portion 20 and the removable cap 30 when the mold is closed and plastic is injected therein, as is commonly referred to as plastic over-molding.

Figure 3:
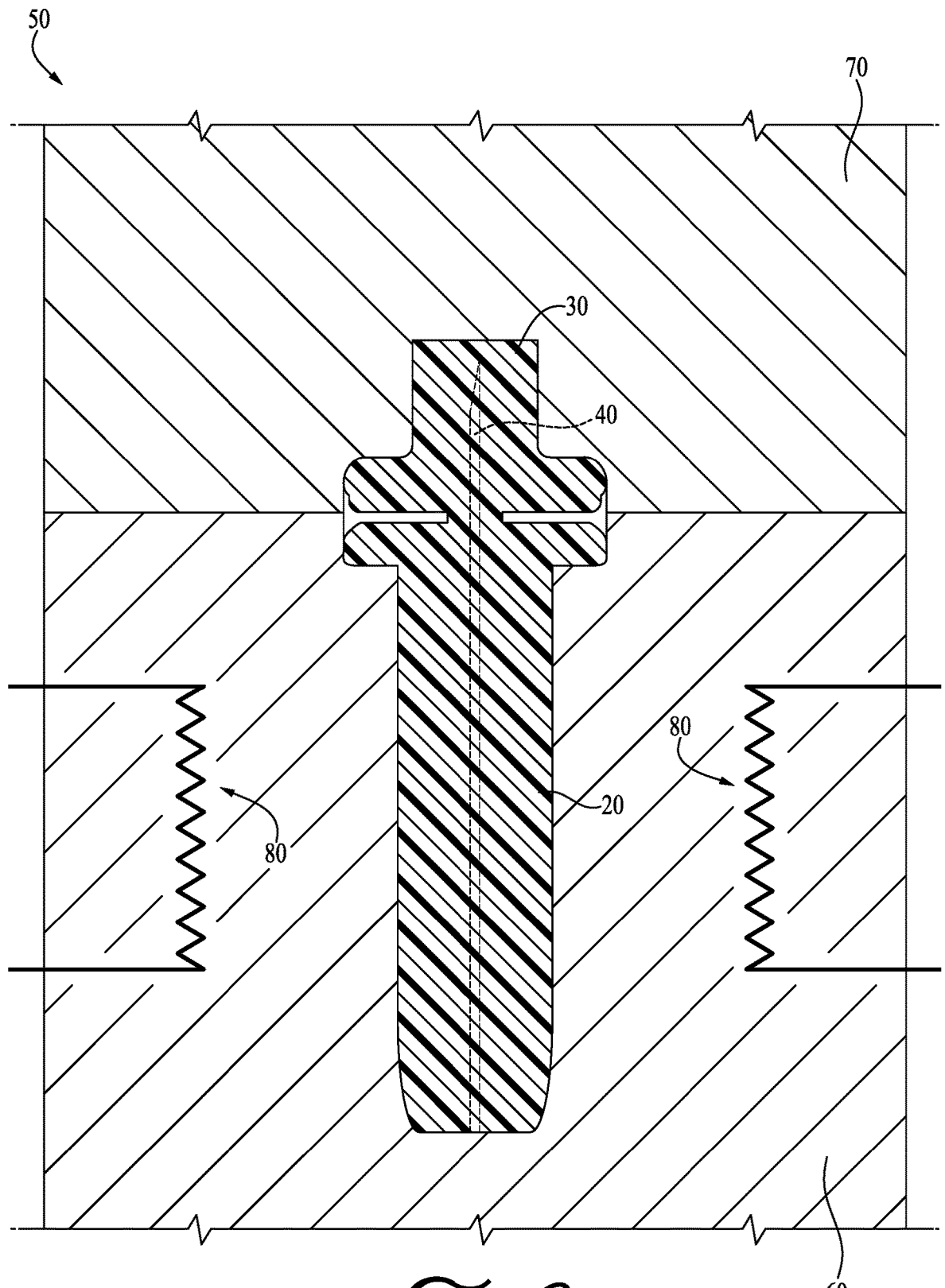
FIG. 3 shows a cross sectional view of the mold of FIG. 2, showing the mold in the closed position wherein the lancet of FIG. 1 is molded within the cavity thereof.

FIG. 3 shows the mold 50 in a closed position wherein the lancet 10 is formed in the cavities 64, 74. Generally, the first and second mold parts 60, 70 abut each other such that the cavities 64, 74 communicate with each other to define a single mold cavity in which the product is to be formed. With the cavities communicating therewith, plastic is injected therein to fill the joined cavities 64, 74 and to entirely encapsulate the needle 40, which in turn forms the lancet 10.

In preferred example embodiments, the needle 40 that is encapsulated in the integrally formed body portion 20 and removable cap 30 is sterilized during the manufacture of the lancet 10, such that a separate post-production sterilization step is not required. In one form, sterilizing the needle 40 during the manufacture of the lancet 10 is accomplished by maintaining at least a specified minimum temperature (e.g., mold temperature) of the mold and/or plastic being injected therein for at least a specified minimum amount of time (e.g., cycle time), effective to sterilize the needle or other embedded object. In example embodiments, the specified minimum temperature of the mold and/or plastic is at least about 370 degrees Fahrenheit (° F.), more preferably at least about 375° F., and more preferably at least about 400° F. The specified amount of time to maintain the specified minimum temperature ("cycle time") is at least about 10 seconds, or alternatively at least about 14 seconds, or alternatively at least about 15 seconds, or alternatively at least about 20 seconds. To maintain the specified minimum temperature, one or more heating elements 80, hot runners, and/or other means of heating the mold may be provided. After maintaining the specified minimum temperature for a specified amount of time, the mold and/or plastic is cooled (allowing the body portion 20 and removable cap 30 to solidify), and the mold 50 is then moved to an open position wherein the lancet 10 is ejected therefrom. Thus, the needle 40 is sterilized during the manufacture of the lancet 10, which eliminates the need for post-manufacturing sterilization.

In an additional example embodiment, the present invention relates to a method for sterilizing a medical device component. The method includes providing a mold; providing a needle within the mold; injecting plastic within the mold to encapsulate the needle, the plastic having a mold temperature; and maintaining the temperature of the plastic at the mold temperature for a cycle time, effective to sterilize the needle or other embedded object. Similarly, according to another example embodiment, the present invention relates to a method for simultaneously manufacturing and sterilizing. The method includes providing a tool; providing a portion of a medical device component within the tool; injecting a plastic within the tool to encapsulate the medical device component, the plastic being at a tool temperature; and maintaining the plastic at the tool temperature for a cycle time effective to sterilize the needle or other embedded object. Additionally, in yet another example embodiment, the present invention relates to a method for manufacturing a sterile lancet. The method includes providing a mold, the mold having a cavity; placing a lancet needle within the cavity; injecting plastic within the cavity to encapsulate the needle therein, the plastic having a mold temperature; and maintaining the plastic at the mold temperature for a cycle time effective to sterilize the needle or other embedded object. The invention also includes a product having a metal component encapsulated with plastic, for example a lancet having a metal needle encapsulated in a plastic lancet body, produced according to any of the methods described herein.

While the invention has been described with reference to preferred and example embodiments, it will be understood by those skilled in the art that a variety of modifications, additions and deletions are within the scope of the invention, as defined by the following claims.

What is claimed is:

1. A mold for manufacturing a product having a metal product component at least partially embedded within a plastic product component, the mold comprising tooling for holding the metal product component, a mold chamber for receiving plastic to form the plastic product component around the metal product component, and means for maintaining a specified minimum mold temperature for a specified minimum cycle time effective to sterilize the metal product component during manufacture, wherein the means for maintaining the specified minimum mold temperature is embedded within the mold adjacent to the mold chamber such that the plastic does not come into direct contact with the means for maintaining the specified minimum mold temperature.

2. The mold of claim 1, wherein the product is a lancet.

3. The mold of claim 1, wherein the mold chamber comprises a lancet body forming portion and a lancet endcap forming portion.

4. The mold of claim 1, wherein the metal product component is a needle.

5. The mold of claim 1, wherein the means for maintaining the specified minimum mold temperature is a heating element.

6. The mold of claim 1, wherein the means for maintaining the specified minimum mold temperature does not protrude into the mold chamber.

7. The mold of claim 1, wherein the tooling comprises a first tooling portion and a second tooling portion.

8. The mold of claim 7, wherein the first tooling portion comprises a first cavity and the second tooling portion comprises a second cavity, the first and second cavities when joined together forming the mold chamber.

9. The mold of claim 8, wherein the means for maintaining the specified minimum mold temperature is embedded in the first tooling portion adjacent the first cavity and does not interfere with the first cavity.

\* \* \* \* \*